US011013956B2

(12) United States Patent
Hyung Jung et al.

(10) Patent No.: US 11,013,956 B2
(45) Date of Patent: May 25, 2021

(54) PORTABLE DEVICE FOR UPPER LIMB REHABILITATION

(71) Applicant: FUNDACION TECNALIA RESEARCH & INNOVATION, Derio-Bizkaia (ES)

(72) Inventors: Je Hyung Jung, Derio-Vizcaya (ES); Cristina Rodriguez De Pablo, Derio-Vizcaya (ES); Aitor Belloso Linacisoro, Derio-Vizcaya (ES); David Valencia Blanco, Derio-Vizcaya (ES); Thierry Keller, Derio-Vizcaya (ES)

(73) Assignee: FUNDACION TECNALIA RESEARCH & INNOVATIION, Derio-Bizkaia (ES)

( * ) Notice: Subject to any disclaimer, the term of this patent is extended or adjusted under 35 U.S.C. 154(b) by 243 days.

(21) Appl. No.: 16/310,972

(22) PCT Filed: Jun. 29, 2017

(86) PCT No.: PCT/EP2017/066208
§ 371 (c)(1),
(2) Date: Dec. 18, 2018

(87) PCT Pub. No.: WO2018/002266
PCT Pub. Date: Jan. 4, 2018

(65) Prior Publication Data
US 2020/0306584 A1 Oct. 1, 2020

(30) Foreign Application Priority Data
Jun. 29, 2016 (EP) .................................. 16382312

(51) Int. Cl.
*A63B 23/12* (2006.01)
*A63B 21/00* (2006.01)
(Continued)

(52) U.S. Cl.
CPC .... *A63B 23/1209* (2013.01); *A63B 21/00178* (2013.01); *A63B 21/00181* (2013.01);
(Continued)

(58) Field of Classification Search
CPC ............ A63B 23/1209; A63B 21/4021; A63B 21/4043; A63B 21/4047; A63B 21/4049;
(Continued)

(56) References Cited

U.S. PATENT DOCUMENTS 316,308 A * 4/1885 Strobel .................. A01F 11/04
460/15
360,069 A * 3/1887 Wardwell ............. A01D 45/021
56/64

(Continued)

FOREIGN PATENT DOCUMENTS

| WO | WO 2005/074371 | 8/2005 |
| WO | WO 2006/047753 | 5/2006 |
| WO | WO 2008/047355 | 4/2008 |

OTHER PUBLICATIONS

European Patent Office, PCT International Search Report and Written Opinion of the Searching Authority, dated Sep. 18, 2017, 13 pages.

*Primary Examiner* — Garrett K Atkinson

(57) ABSTRACT

The invention refers to a portable device (100) for upper limb (2, 3) rehabilitation which is movable over a surface, usually a flat horizontal surface, and which comprises means for detecting an intention to move from the user (1), thereby providing assistance/resistance to perform the right movement just when needed, especially when the goal movement is non-deterministic.
Additionally, the portable device (100) of the invention comprises a support structure for the forearm of a user (which can be similar to an armrest) which is pivotable, preferably in a direction of the rotational joint of elbow (it
(Continued)

pivots vertically around a horizontal axis), thereby allowing free ergonomic elbow and shoulder flexion/extension, but restricting shoulder rotation, which is determined by the orientation of the device in order to avoid injuries.

The invention further refers to a method for rehabilitating an upper limb (2, 3) of a user (1), and to a rehabilitation system for an upper limb (2, 3) of a user (1), comprising such portable device (100).

15 Claims, 8 Drawing Sheets

(51) Int. Cl.
  *A63B 23/035*    (2006.01)
  *A63B 24/00*    (2006.01)
  *A63B 22/00*    (2006.01)

(52) U.S. Cl.
  CPC ...... *A63B 21/4021* (2015.10); *A63B 21/4049* (2015.10); *A63B 23/03508* (2013.01); *A63B 24/0003* (2013.01); *A63B 2022/0094* (2013.01); *A63B 2220/16* (2013.01); *A63B 2220/51* (2013.01)

(58) Field of Classification Search
  CPC ........ A63B 21/00178; A63B 21/00181; A63B 23/03508; A63B 24/0003; A63B 2022/0094; A63B 2220/16; A63B 2220/51; A63B 2024/0065; A63B 2024/0096; A63B 5/11; A63B 5/4528; A63B 21/0058; A63B 5/1071; A63B 24/0075; A61H 2201/1215; A61H 2201/1638; A61H 2201/1659; A61H 1/0274; A61H 2001/0207; A61H 2201/0157
  See application file for complete search history.

(56) References Cited

U.S. PATENT DOCUMENTS

| | | | | |
|---|---|---|---|---|
| 2,475,656 | A * | 7/1949 | Bidak | A63B 21/06 482/46 |
| 3,740,033 | A * | 6/1973 | Kamp | A63B 21/015 482/115 |
| 3,982,755 | A * | 9/1976 | Sarich | A63B 23/14 482/93 |
| D264,237 | S * | 5/1982 | McCaleb | 482/46 |
| 4,438,920 | A * | 3/1984 | Veillette | A63B 23/14 482/46 |
| 4,998,721 | A * | 3/1991 | Anders | A63B 21/0783 482/4 |
| 5,244,444 | A * | 9/1993 | Wostry | A63B 21/0615 482/109 |
| 5,312,309 | A * | 5/1994 | Fox | A63B 21/0004 482/120 |
| 5,871,423 | A * | 2/1999 | Pruchnik | A63B 21/22 482/110 |
| 5,967,949 | A * | 10/1999 | Davenport | A63B 21/153 482/108 |
| 6,099,437 | A * | 8/2000 | DeMers | A63B 23/14 482/46 |
| 6,117,093 | A * | 9/2000 | Carlson | A63B 21/0056 482/4 |
| 6,234,934 | B1 * | 5/2001 | Gorczyca | A63B 21/0609 482/108 |
| 6,477,448 | B1 * | 11/2002 | Maruyama | B25J 13/02 700/302 |
| D505,459 | S * | 5/2005 | Lagattuta | D21/680 |
| 7,028,682 | B1 * | 4/2006 | Hansen | A63B 69/407 124/16 |
| 7,029,423 | B2 * | 4/2006 | Lear, Jr. | A63B 21/06 482/40 |
| 7,753,827 | B1 * | 7/2010 | Emick | A63B 23/14 482/44 |
| 7,837,599 | B2 * | 11/2010 | Kowalczewski | G09B 19/003 482/44 |
| 8,221,049 | B1 * | 7/2012 | Westendorf | E02F 3/404 414/729 |
| 8,636,630 | B2 * | 1/2014 | Morris | A63B 21/4047 482/117 |
| 8,834,169 | B2 * | 9/2014 | Reinkensmeyer | A61H 1/0274 434/247 |
| 8,915,828 | B1 * | 12/2014 | Stalnaker | A63B 23/1209 482/131 |
| 9,375,598 | B1 * | 6/2016 | Lai | A61H 1/0274 |
| 9,522,294 | B1 * | 12/2016 | Kangatharalingam | A63B 21/0609 |
| 9,827,677 | B1 * | 11/2017 | Gilbertson | B25J 15/0014 |
| 9,827,678 | B1 * | 11/2017 | Gilbertson | B25J 18/025 |
| 10,201,901 | B2 * | 2/2019 | Sato | B25J 9/1694 |
| 10,300,331 | B2 * | 5/2019 | Seltzer | A63B 21/4033 |
| 10,384,096 | B1 * | 8/2019 | Aery | A63B 23/1209 |
| 2003/0028130 | A1 * | 2/2003 | Wunderly | A63B 21/00181 601/5 |
| 2006/0276315 | A1 * | 12/2006 | Krietzman | A63B 21/015 482/114 |
| 2007/0239315 | A1 * | 10/2007 | Sato | B25J 9/1612 700/245 |
| 2007/0265146 | A1 * | 11/2007 | Kowalczewski | A63B 23/03525 482/92 |
| 2011/0287907 | A1 * | 11/2011 | Morris | A63B 23/1209 482/117 |
| 2013/0226341 | A1 * | 8/2013 | Sturm | B25J 5/007 700/245 |
| 2014/0316308 | A1 * | 10/2014 | Lee | A61H 1/0274 601/33 |
| 2015/0104283 | A1 * | 4/2015 | Nogami | B25J 9/06 414/730 |
| 2015/0360069 | A1 * | 12/2015 | Marti | A63B 23/03508 482/6 |
| 2016/0096653 | A1 * | 4/2016 | Stratton | B65G 65/32 414/332 |
| 2018/0126205 | A1 * | 5/2018 | Rogers | F16B 21/186 |
| 2018/0214740 | A1 * | 8/2018 | Horen | A63B 21/4035 |
| 2018/0361200 | A1 * | 12/2018 | Walker | A63B 21/4034 |

* cited by examiner

PORTABLE DEVICE FOR UPPER LIMB REHABILITATION

TECHNICAL FIELD

The present invention relates to a portable device for rehabilitating an impaired user having difficulties in executing simultaneous reaching and lifting tasks with the upper limb. The device is in particular suitable for use in rehabilitation and/or physical therapy programs for the treatment of neuro-vascular or musculoskeletal injuries or diseases of the upper limb.

STATE OF THE ART

Hundreds of thousands of people are disabled each year because of upper limb motor impairments. Impairment can be due to neurological diseases such as stroke, or can be due to musculoskeletal injuries. In both cases the disease or injury can result in a decreased range of motion, muscular weakness, loss of speed and/or reduced coordination of the affected limb.

Physical therapy is known to be effective in reducing the degree of disability. In fact, better results in terms of rehabilitation outcome are obtained in care centres where patients receive more therapy per day for extended periods of time.

An intelligent robot mechanically coupled with the arm of the patient can be used to help the patient carrying out exercises during the rehabilitation period, thus increasing the time spent in rehabilitation training. Moreover, the sensors of the robot can be used to assess the degree of the impairment at the beginning of the therapy cycle and to monitor the progresses.

However, the present generation of rehabilitation robots still presents several unsolved issues that prevent it from being used on a large scale. Among them, cost is an important one. The robotic device should be cheap enough to be widely adopted by care centres. Simplicity of use is also an issue not only for therapists, commonly with non-engineering background but also for the patients in case the robotic device has to be used at home by themselves. The "use-at-home" feature asks also for portability of the device.

A number of devices try to solve this issue. For instance, patent document US-2007/0021692-A1 describes a system for performing induced limb movements. Hand or foot trajectories are recorded by means of position sensors, and the pressure exerted by the limb can be recorded.

Patent document WO 99/61110 describes a system for the training of quick reach movements (feed forward movements). The system incorporates position measurement (hand, arm, joints), EMG measurement and feedback to the user.

Patent document U.S. Pat. No. 7,311,643-B2 describes a portable upper limb and shoulder exercise board. It provides means to move a handle in a plane with a discretely variable friction coefficient.

Patent document JP 2002-272795 describes an upper limb rehabilitation device that includes a measurement of position and force exerted by the user on grip (transportation device), and feedback means. The system requires an instrumented table with tracks over which the transportation device can move.

Patent document JP 2004-008605 describes a limb rehabilitation training apparatus. It provides means to measure the force exerted by a limb on a fixed device together with means to provide feedback to the user, such as video, sound, vibration.

Patent document EP-2298266-A1 discloses a portable device for upper limb rehabilitation which is movable over a surface and which comprises an armrest for the forearm of the user. The device furthermore comprises means for monitoring the movement of the armrest and means for sensing a force exercised by the arm of the user in an orthogonal direction to the surface, i.e, the vertical direction.

Patent document EP-2678759-A1 discloses a haptic device that is movable on wheels and is capable of following any desired trajectory or path, i.e., it is omnidirectional.

In the two latter cases, the forearm of the user is constrained to move only in a horizontal plane (i.e. the plane of the surface, which is also that of the support), so neither natural elbow flexion nor natural elbow extension is freely allowed during planar reaching tasks. Also, constant shoulder flexion is required, which in addition to be tiring for the patient, it may be harmful and/or reduce arm training efficacy due to trunk motion inevitably occurring so as to compensate for the constant shoulder flexion.

In order that these devices provide the necessary therapeutic outcome, active involvement of the patient in training is highly important in order to maximize training efficacy. In this respect, gaming is renowned for its ability to provoke high levels of engagement and hold attention for long periods of time; thus, incorporating gaming into stroke rehabilitation treatments has been widely accepted in the past years. There is evidence that the use of gaming may be beneficial in motor function improvement when compared with conventional therapy. However, when providing assistance for those subjects who cannot perform the movements themselves, the motivation and cooperation is lost unless some assistance is provided to the severely impaired user just when needed.

It is relatively easy to implement this assistance when the movement to be assisted is known, i.e. deterministic movement: it is possible to configure the device so as to assist the movement when the user is not able to fulfil it, or to offer resistance when the movement is not the right one. However, when it is not known where the patient wants to move to, i.e. non-deterministic movement (for example, when completing a jigsaw puzzle), it is not evident to provide the necessary assistance to the user. In fact, detecting the user's intention is needed.

Current systems for detecting the user's intention use complex and expensive sets of sensors, which prevents them from being used on a large scale.

Thus, a cost-effective dedicated device for patients with severe impairment is demanded for detecting their intention to move, so that the patient somehow controls the device, not being controlled by it, and is therefore actively involved in the therapy, taking into account the rehabilitation purpose and the finding that these patients' intention might not be shown in the right way'.

DESCRIPTION OF THE INVENTION

In order to avoid the problems indicated in the previous section, the invention provides a portable device for upper limb rehabilitation which is movable over a surface (usually a flat horizontal surface), and which comprises means for detecting an intention to move from the user (i.e. the patient), thereby providing assistance/resistance to perform the right movement just when needed, especially when the goal movement is non-deterministic.

Additionally, the portable device of the invention comprises a support structure for the forearm of a user (which can be similar to an armrest) which is pivotable, preferably in a direction of the rotational joint of elbow (it pivots vertically around a horizontal axis), thereby allowing free ergonomic elbow and shoulder flexion/extension, but restricting shoulder rotation, which is determined by the orientation of the device in order to avoid injuries.

The present invention refers to a portable device for rehabilitating an upper limb of a user, the portable device comprising a support which is movable over a surface, the portable device further comprising:

a first support structure for supporting a forearm of the user; and monitoring means for monitoring the movement of the support.

According to a first aspect of the invention, the portable device further comprises a second support structure; the first support structure being coupled to the second support structure by means of a first joint having one rotational degree of freedom; and the second support structure being coupled to the support by means of a second joint having three rotational degrees of freedom; the portable device further comprising:

force sensing means for sensing a force exercised by an arm of the user on the support;

angle sensor means for measuring an angle of inclination of the first support structure with respect to the second support structure; and processing means for detecting a movement intention of the user based on the force measured by the force sensing means and on the angle of inclination of the first support structure measured by the angle sensor means.

As will be explained further below, the processing means may be further configured to compute an intention vector which defines a direction of the user's movement intention based on data provided by the angle sensor means and by the force sensing means and by, preferably also based on an orientation of the portable device on the surface.

The specific mechanical design of the first and second support structures in the portable device allows natural and secure arm movements, avoiding undesirable movement patterns that could lead to injuries, and also permits detecting the user's intention to move, which in turn maximises the therapeutic outcome by promoting active involvement of the user in the training.

As indicated, the first support structure is coupled to the second support structure by means of a first joint having one rotational degree of freedom, this one rotational degree of freedom preferably being pitch, that is, the first support structure is pivotable vertically with respect to the second support structure.

In preferred embodiments the first support structure comprises first fastening means for fastening at least the forearm of a user, thereby controlling the position and configuration of the arm, specifically the abduction/adduction and rotation movements of the shoulder, and therefore preventing shoulder dislocation.

Therefore, the portable device of the present invention allows a patient to conduct natural forearm movements during planar reach tasks, not only with minimal resistance but also without moving the trunk and with a natural posture of the arm.

The first support structure preferably further comprises second fastening means for fastening a wrist or a hand of the user, the first and second fastening means being located at separate points on the first support structure which define a first direction F'-B' coinciding with the longitudinal axis of the forearm of the user when attached to the portable device.

In preferred embodiments the force sensing means are located between the second support structure and the support; since the second support structure is freely rotatable with respect to the support of the portable device, the force sensing means are able to detect a force applied by the user on the second support structure.

In some embodiments the force sensing means are at least two load cells, to provide further information on the force (direction and magnitude) applied by the user. Depending on the dimensions of the second support structure, the load cells may be placed parallel to the first direction F'-B'.

The force sensing means are preferably symmetrically placed on the support with respect to a plane parallel to the first direction F'-B' which contains the first and second fastening means, so as to facilitate implementation of the detection of the user's intention to move.

In some embodiments the angle sensor means to measure the rotation angle of the first support structure is a potentiometer, which provides reliable information with low cost and is simple to include in the device.

The processing means for detecting a movement intention of the user are configured to determine an intention of the user to move in a first direction F'-B' and in one sense or the opposite within that first direction based on a value of the angle of the first support structure and its sign, respectively, as provided by the angle sensor means.

The processing means for detecting a movement intention of the user may be further configured to determine an intention of the user to move in the first direction F'-B' based on the angle of the first support structure and on the force measured by the force sensing means when the angle of the first support structure is above a pre-established value.

The processing means for detecting a movement intention of the user may be configured to determine an intention of the user to move in a second direction L'-R', which is orthogonal to the first direction F'-B', based on the force measured by the force sensing means.

In some embodiments, the portable device is motorised, so as to provide assisted movement to the user to move in a specific direction once the movement intention is detected. The motorisation of the portable device may consist in motorising the first support structure and/or the second support structure and/or the first joint and/or the second joint.

A further aspect of the invention refers to a method for rehabilitating an upper limb of a user, the method comprising:

attaching at least a portion the upper limb (usually the forearm) of the user to a portable device as defined in the foregoing;

monitoring the movement of the support of the portable device;

measuring a force exercised by the upper limb of the user on the support;

measuring an angle of inclination of the first support structure with respect to the second support structure; and determining a movement intention of the user based on the force measured by the force sensing means and on the angle of the first support structure.

In preferred embodiments, once the movement intention is determined, the method further comprises providing assisted movement, usually motorised, to the user.

A further aspect of the invention refers to a rehabilitation system for an upper limb of a user, the system comprising:

a portable device as defined in the foregoing;

a remote control and visualization unit; and a training and assessment unit, which is configured to provide a training session; wherein the training and assessment unit is configured to determine a target position and orientation of the upper limb of the user based on an intention vector provided by the processing means and a set of possible target positions of the training session.

The training and assessment unit may be implemented as an independent unit from the portable device. Or the training and assessment unit may be integral with or part of the processing unit of the portable device, the processing unit being further configured to determine the target position.

The rehabilitation system may further comprise a map of the surface over which the portable device moves, in order to detect position and orientation of the portable device thereon.

In case the portable device is motorised, the training and assessment unit is further configured to provide assisted movement to the upper limb to reach the target position.

The different aspects and embodiments of the invention defined in the foregoing can be combined with one another, as long as they are compatible with each other.

Additional advantages and features of the invention will become apparent from the detailed description that follows and will be particularly pointed out in the appended claims.

BRIEF DESCRIPTION OF THE DRAWINGS

To complete the description and in order to provide for a better understanding of the invention, a set of drawings is provided. Said drawings form an integral part of the description and illustrate an embodiment of the invention, which should not be interpreted as restricting the scope of the invention, but just as an example of how the invention can be carried out. The drawings comprise the following figures.

DESCRIPTION OF A WAY OF CARRYING OUT THE INVENTION

Figure 1:
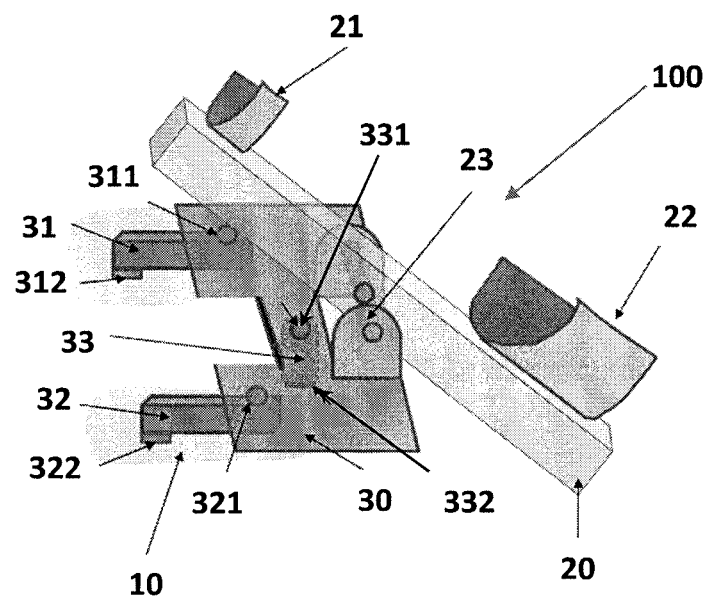
FIG. 1 is a schematic perspective view of the upper portion of a portable device for arm rehabilitation in accordance with an exemplary embodiment of the present invention.
Figure 2:
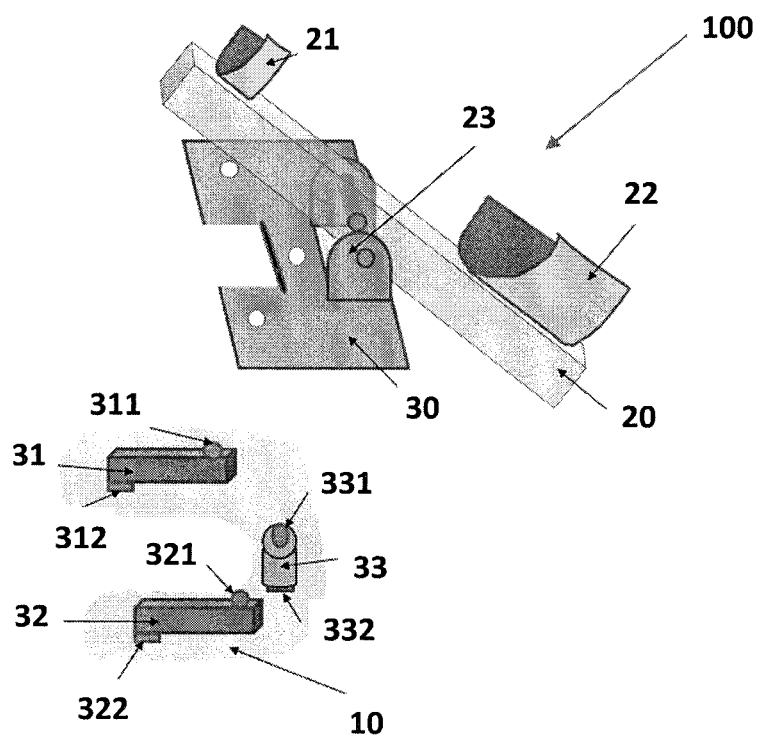
FIG. 2 is an exploded view of the portable device shown in FIG. 1.

The following description is not to be taken in a limiting sense but is given solely for the purpose of describing the broad principles of the invention. Embodiments of the invention will be now described by way of example, with reference to the above-mentioned drawings showing elements and results according to the invention.

Referring now to the Figures, an exemplary embodiment of the portable device 100 according to the invention will be described. The portable device (also referred to in this description as mobile unit or mobile robot) includes a support 10 (also referred to in this description as mobile platform) and is movable over a surface, usually a flat horizontal surface (not shown in the Figures), like that of a table.

Therefor, the portable device comprises means for such movement over the flat surface, which may consist in three spherical wheels such as an omnidirectional wheel (not shown in the drawings), preferably arranged at the vertexes of an equilateral triangle.

Figure 3:
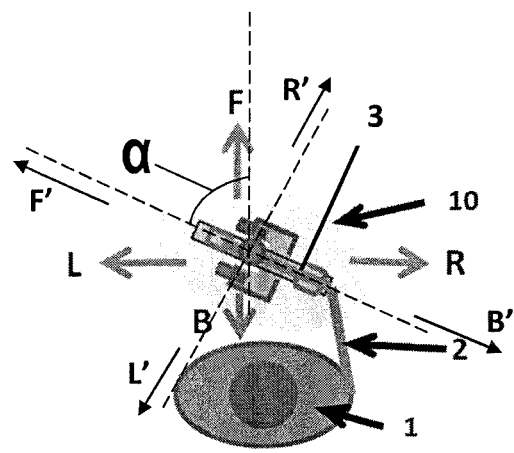
FIG. 3 is a schematic top view of the portable device of FIG. 1 attached to the forearm of a user.
Figure 4:
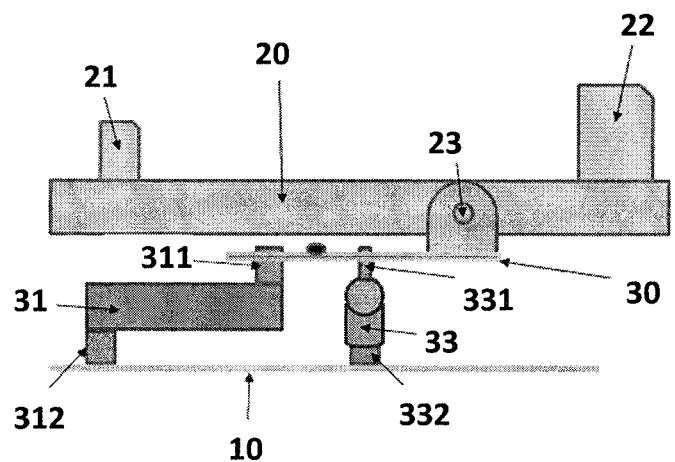
FIG. 4 is a side view of the portable device of FIG. 1 in a neutral position.

The portable device 100 of the invention is for rehabilitating an upper limb—arm 2, forearm 3—of a user 1, and it further comprises an armrest 20, which has a hand orthosis 21 and a forearm orthosis 22, whereto the hand and/or wrist and forearm 3 of a user can be fastened (cf. FIG. 3).

Once the portable device 100 is attached to the forearm of the user, it is movable in any direction over the surface where the user 1 does their rehabilitation exercises, usually following the cues prompted to him/her by means of a screen (not shown in the Figures) located in front of the user. The portable device 100 enables the user to do various movements in a large workspace on the horizontal surface.

Referring now to FIG. 3, for reference purposes, the movements of the portable device 100 will be referred to the following directions:

absolute forward F and absolute backward B, that is, a direction F-B defined by the position of the user and that of the screen;

absolute rightward R and absolute leftward L, that is, a direction L-R orthogonal to the absolute forward-backward direction F-B defined in the previous sentence;

relative forward F' and relative backward B', that is, in a direction F'-B' parallel to a longitudinal axis of the armrest 20; and relative rightward R' and relative leftward L', that is, a direction L'-R' orthogonal to the longitudinal axis of the armrest 20.

In the preferred embodiment shown in the drawings, the armrest 20 is connected to a plate 30 in a pivotable manner by means of a horizontal joint 23, the armrest 20 thus being pivotable (angle Θ, cf. FIG. 5) in a plane orthogonal to that of the support 10 (or the surface over which the portable device 100 moves) in the relative F'-B' direction. This is important for facilitating natural arm movement as it allows free flexion-extension movements of the elbow.

The angle of the armrest 20 in the horizontal plane corresponds to the angle of the portable device 100, which allows controlling the armrest angle α, and consequently the forearm angle, in the horizontal plane. This specific structure of the portable device 100 allows natural and secure arm movements, avoiding undesirable shoulder movements that could lead to injuries by controlling the angle of the portable device 100

The portable device 100 also includes a potentiometer (not shown in the drawings) or any other suitable angle sensor means mounted on the horizontal joint 23 for measuring the rotation angle Θ of the armrest 20.

The portable device 100 also includes an optical tracking device, which is embedded in the support 10, so that the absolute position and orientation (given by angle α, cf. FIG.

3) of the portable device 100 is known and can be computed at all times. Other suitable means for computing the position and orientation of the portable device 100 can be included in the portable device.

The portable device 100 further includes two load cells 31, 32 which are located between the plate 30 and the support 10. In the preferred embodiment shown in the Figures, the load cells 31, 32 are placed in parallel with the longitudinal axis of the armrest 20, preferably at equal distances from the armrest 20. Symmetric locations of the load cells 31, 32 are preferred, since an asymmetric may require calibration of the load cells before using them. For simplicity, equal distance is recommended.

One side of each load cell is connected to the plate by means of a screw (screws 311 and 321) and the other side is mounted on an upper side of the support 10 also by means of a screw (screws 312 and 322).

In addition, the portable device 100 comprises a joint 33 having three rotational degrees of freedom, such as a universal joint, which is connected to a lower side of the plate 30. The universal joint 33 is aligned with the armrest 20 and preferably at its geometrical centre, by means of a screw 331 so that rotation of the plate 30 in any direction is permitted in response to a force applied by the forearm, resulting in the load cells 31, 32 being deflected. The universal joint 33 is connected to the upper side of the support 10 by means of a screw 332.

The support 10 hosts an embedded processing unit (not shown in the drawings), that preferably comprises means for receiving analogue and/or digital inputs, as well as sending digital outputs, means for controlling and driving the wheels, and means for wired/wireless communications.

Figure 5:
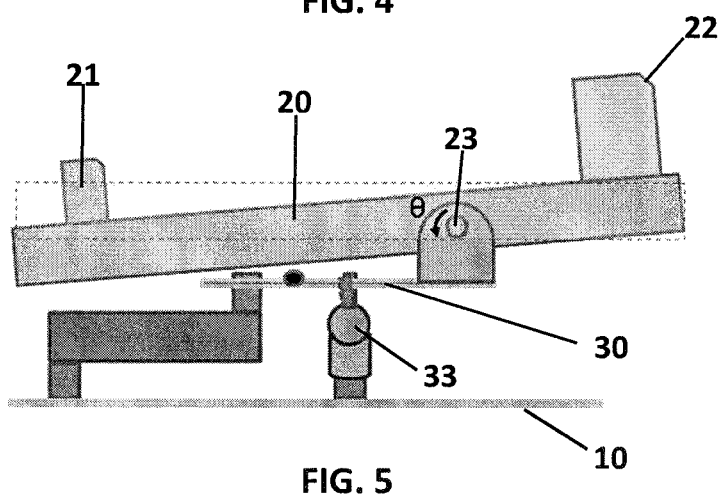
FIGS. 5 and 6 show side views of the portable device of FIG. 1, slightly tilted forward and backward, respectively.
Figure 6:
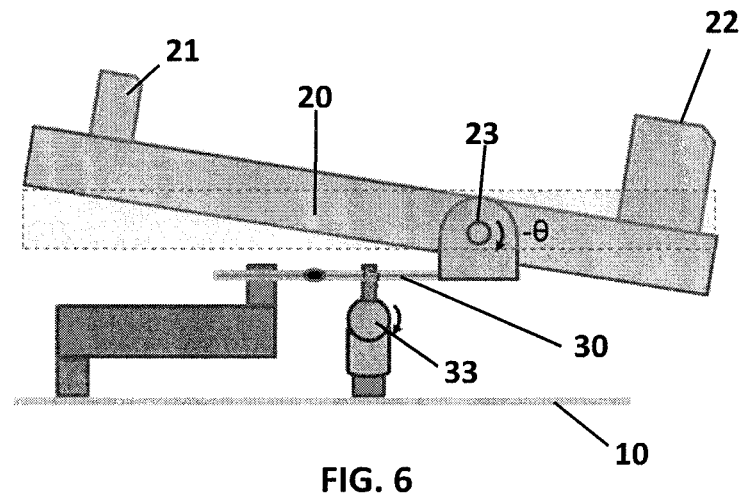

In order to detect the user's intention to move the portable device 100 forward and/or backward F-B, the processing unit makes use of the following inputs: the armrest rotation angle Θ as measured by the potentiometer, the force signals as measured by the two load cells 31, 32 and the relative orientation of the portable device 100 over the surface as given by angle α, provided by the optical tracking device. Since the armrest horizontal joint 23 is a freely rotatable joint, even a weak force applied by the user 1 can make the armrest 20 move, resulting in an angle change in the intended direction as shown by FIGS. 5 and 6. This change in the rotation angle Θ of the armrest 20 is detected by the potentiometer.

Figure 7:
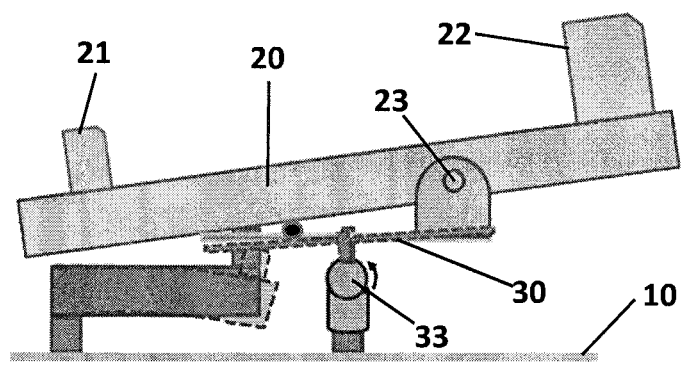
FIGS. 7 and 8 show side views of the portable device of FIG. 1, further tilted forward and backward, respectively, with respect to tilt shown in FIGS. 5 and 6.
Figure 8:
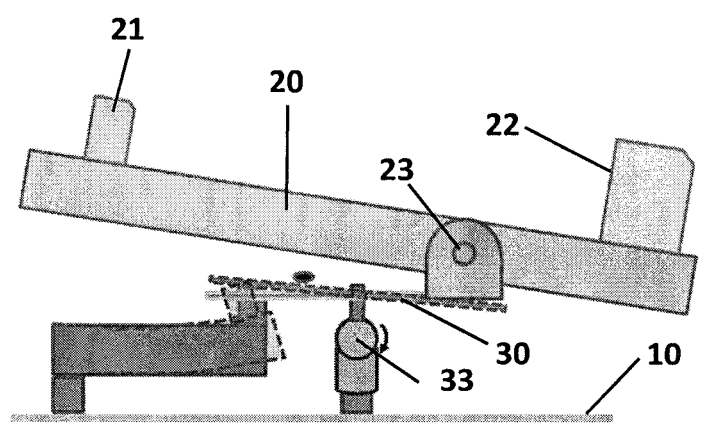

But, as shown in FIGS. 7 and 8, there is a situation in which the rotation angle Θ of the armrest does not change any more, even if the user continues applying force either relative forward F' or relative backward B': when the armrest 20 makes contact with the plate 30, which depends on the design and dimensions of the plate 30 and of the armrest 20. Alternatively, the rotation angle Θ of the armrest can be mechanically restricted to a maximum value. In this situation, the user's intention to move in the relative forward-backward direction F'-B' is detected by the information provided by the load cells 31, 32. Once the armrest makes contacts the plate 30 or the armrest rotation angle Θ reaches its maximum value, the two load cells 31, 32 are deflected in response to the force applied by the patient. In the specific design of the portable device shown in the Figures, if both forces are positive, the movement intention is relative forward F', while if the forces are negative it is indicative of a relative backward B' movement intention.

Figure 11:
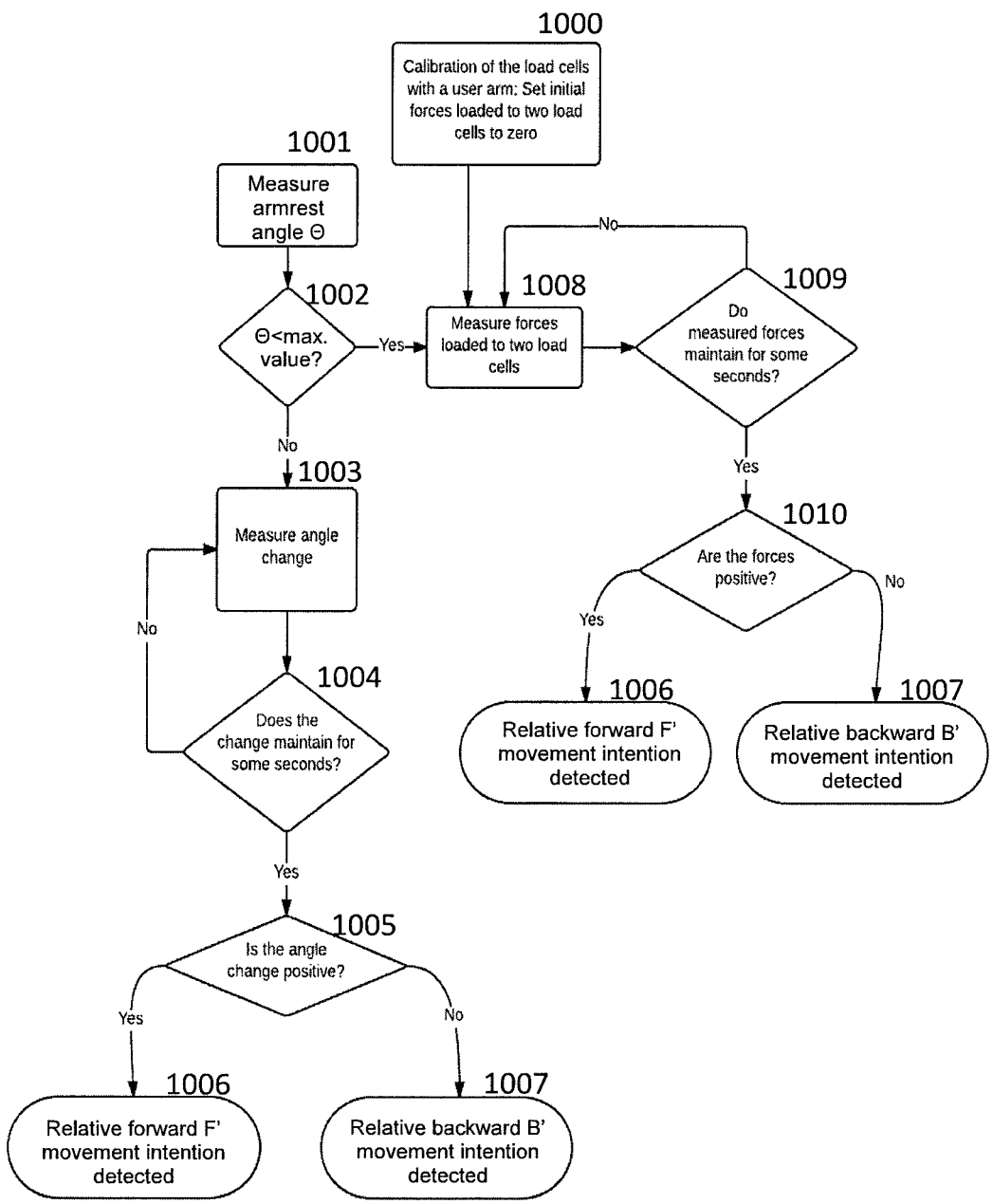
FIG. 11 is a flowchart showing how the user's intention to move in a relative forward/backward direction is detected.

FIG. 11 summarises how movement intention in the relative forward/backward direction F'-B' is detected.

First, once the forearm 2 of the user 1 is attached to the armrest, the load cells 31, 32 are calibrated (1000) to take into account the weight of the user's forearm, and the forces measured by the load cell are set to zero. Then the rotation angle of the armrest 20 is measured (1001). It is then checked (1002) whether this angle is below its maximum value or not. If it has not reached its maximum value, then the change in the rotation angle is measured (1003), and it is checked (1004) whether this angle change lasts for at least a predetermined time interval, otherwise the change in the rotation angle is measured again. If the change in the rotation angle lasts in time (that is, it is not due to the patient trembling), the rotation angle is measured (1005) and depending on whether it is positive or negative it is decided that the intention to move is in the relative forward F' (1006) or in the relative backward B' (1007), respectively.

If the rotation angle has reached its maximum value (1002), then the forces in the two load cells are measured (1008), and it is checked (1009) whether these forces last for at least a predetermined time interval, otherwise the force are measured again. If the force measured by the load cells lasts in time (is not due to the patient trembling), it is checked (1010) whether they are positive or negative (with respect to the zero value set during the calibration phase), and it is decided that the intention to move is relative forward F' (1006) or relative backward B' (1007), respectively. By positive it is meant that the force measured by the load cells is higher than the initial force measured by the load cells with the user's forearm in the calibration phase.

Figure 9:
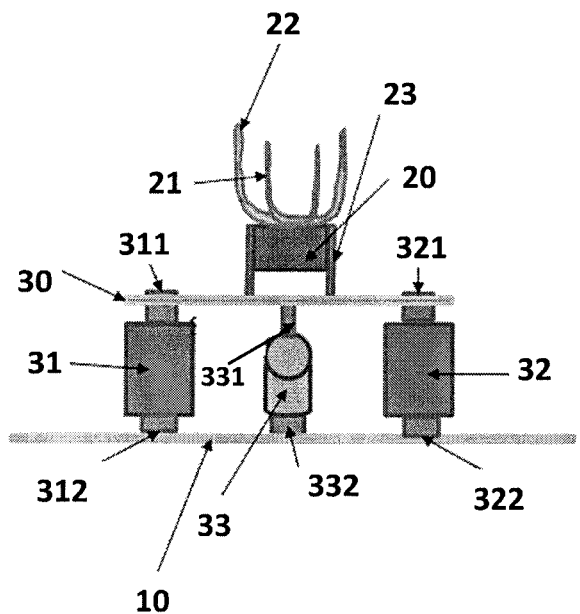
FIGS. 9 and 10 show front views of the portable device of FIG. 1, in a rest position and slightly tilted sidewards, respectively.
Figure 10:
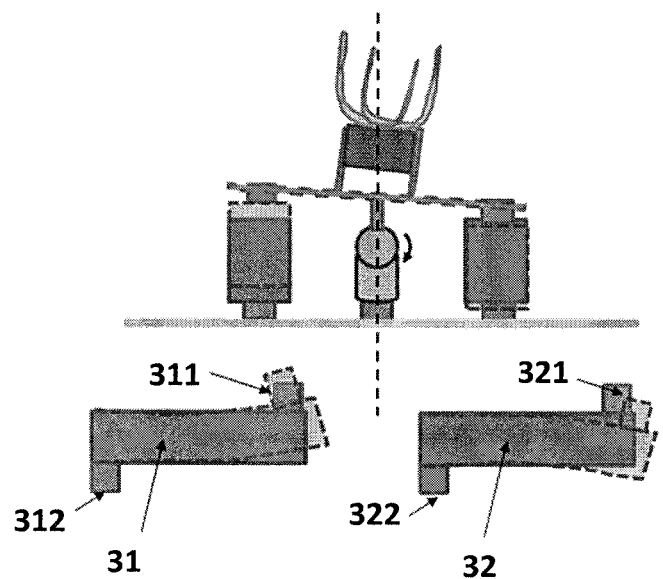

In order to detect the user's intention to move in the relative rightward/leftward direction L'-R', relative to the portable device 100, the processing unit makes use of the force signals provided by the two load cells 31, 32. As in the previous case, first a calibration phase 1000 is carried out. When the patient applies forces in the L'-R' direction to the armrest 20, these forces are directly transferred to the two load cells 31, 32 through the plate 30 which is rotatable with respect to the universal joint 33, as shown in FIGS. 9 and 10. When a relative leftwards L' force is applied to the armrest 20, a negative force is measured by the load cell 31 whereas a positive force is measured by the load cell 32. On the contrary, when a relative rightward R' force is applied to the armrest 20, a positive force is measured by the load cell 31 while the force measured by the load cell 32 is negative.

Figure 12:
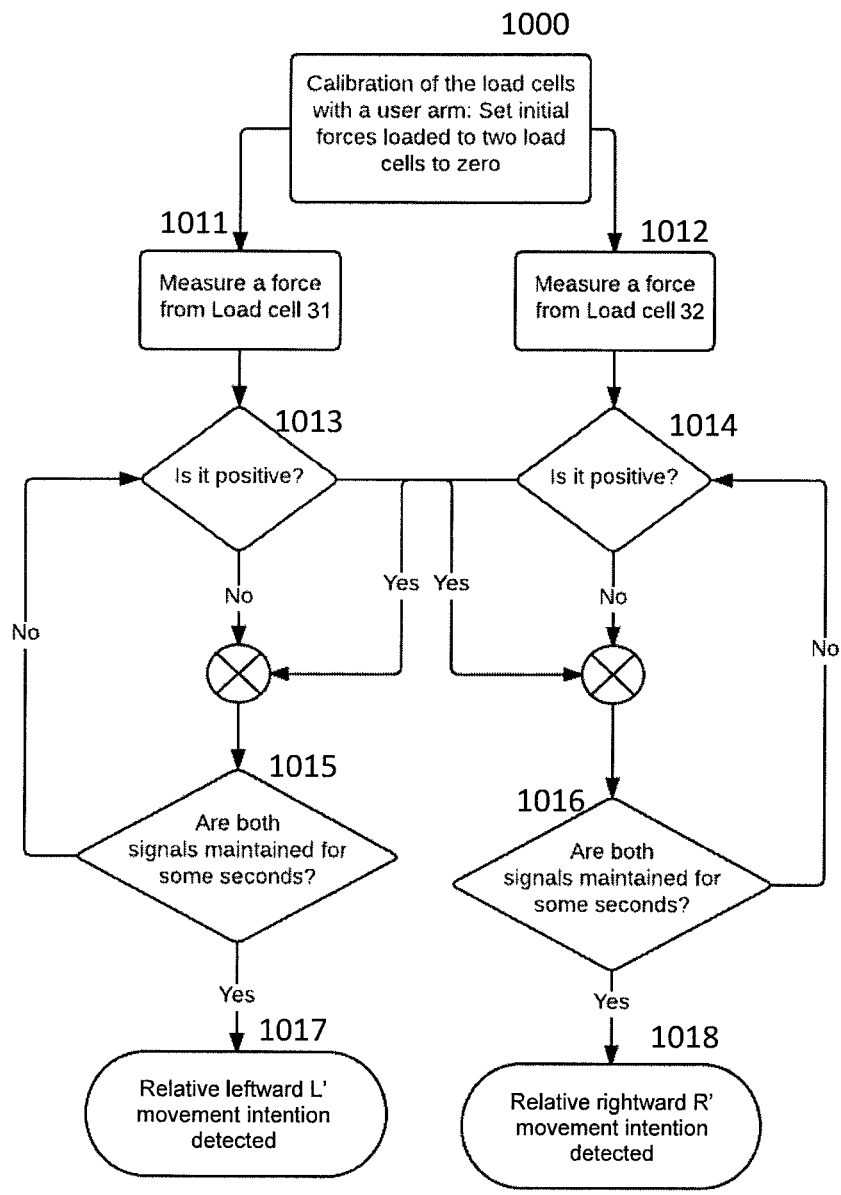
FIG. 12 is a flowchart showing how the user's intention to move in a relative leftward/rightward direction is detected.

FIG. 12 summarises how the intention to move is detected in the relative leftward-rightward direction L'-R'.

The forces from load cells 31, 32 are measured (1011, 1012). It is then checked (1013, 1014) whether the force measured at each load cell is positive or negative (with respect to the zero value set during the calibration phase). It is then checked (1015, 1016) whether the force measurements last for at least a predetermined time interval, otherwise the forces are measured again. Then, when a negative force is measured by the load cell 31 and a positive force is measured by the load cell 32 it is decided that the intention to move is relative leftward L' (1017); if the load cell 31 measures a positive force and the load cell 32 measures a negative force, it is decided that the intention to move is relative rightward R' (1018).

As indicated before, the condition of checking the duration of the signals is needed to ensure whether the signals are generated intentionally or not, since most stroke patients have some tremor, which may affect the signals.

Figure 13:
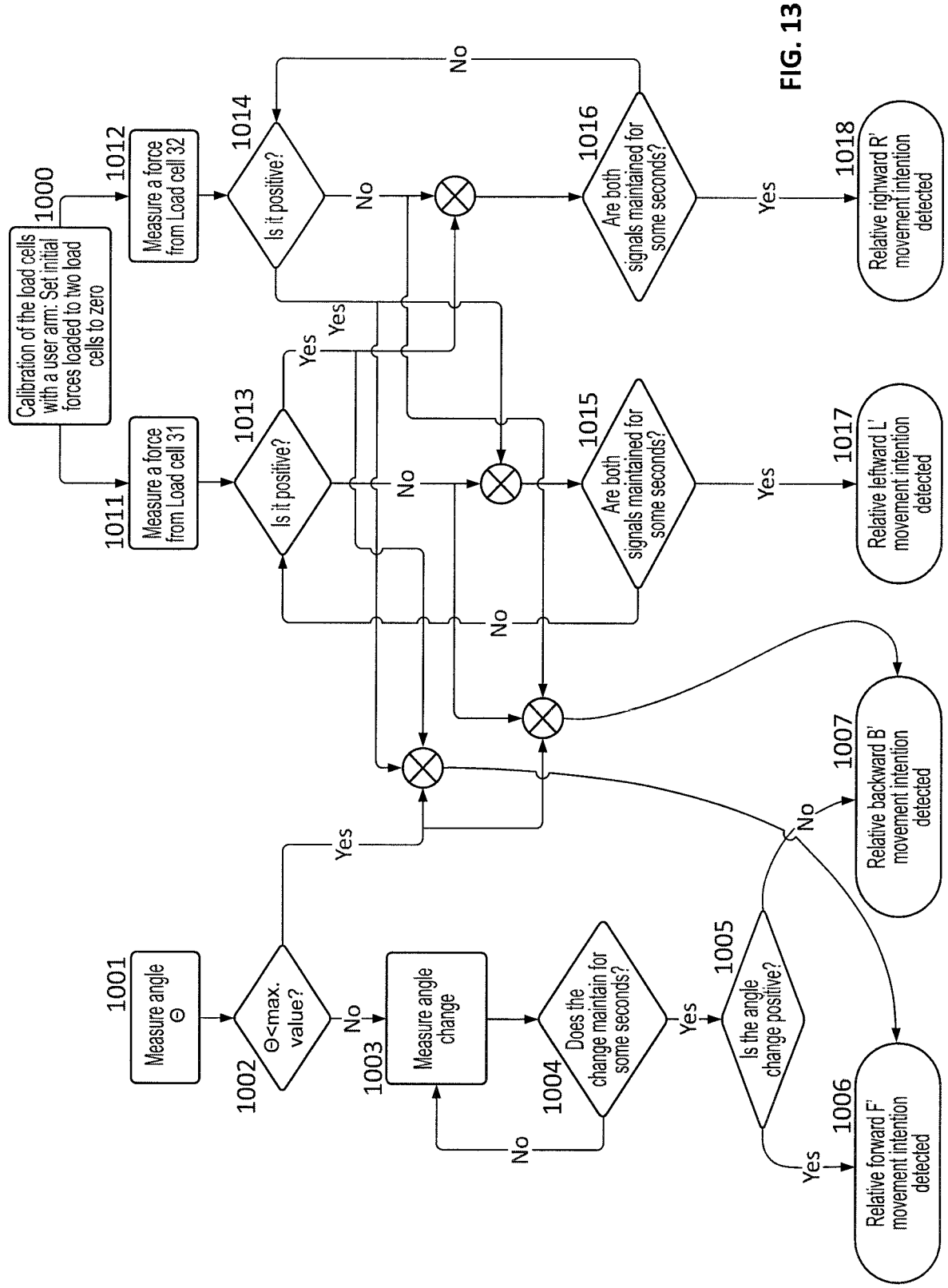
FIG. 13 is a flowchart showing the operational principle to detect the user's intention to move.

FIG. 13 is a flow diagram showing the overall process for detecting the user's intention to move. The steps of the decision process correspond to those of FIGS. 11 and 12, step 1008 in FIG. 11 corresponding to steps 1011 and 1012 in FIG. 13; similarly, decision step 1009 in FIG. 11 corresponds to decision steps 1015 and 1016 in FIG. 13, and decision step 1009 in FIG. 11 corresponds to decision steps 1013 and 1014 in FIG. 13.

Once the user's intention to move in the relative directions F'-B' and L'-R' has been detected, it is possible to heuristically detect the user's intention to move in the absolute directions F-B and R-L based on the orientation a of the portable device 100 on the surface and the detected relative directions F'-B' and L'-R. A counter clockwise rotation of relative forward F' with respect to absolute forward F indicates positive angle of α.

The movement intention in the absolute directions is detected as follows:

If $-30°<\alpha<30°$, then:
If F' is detected, it indicates the user is trying to move in the absolute forward F direction.
If B' is detected, it indicates the user intents to move in the absolute backward B direction.
If R' is detected, it indicates the user intents to move in the absolute rightward R direction.
If L' is detected, it indicates the user intents to move in the absolute leftward L direction.

If $30°<\alpha<60°$, then:
If F' and R' are detected at the same time, it indicates the user intents to move in the absolute forward F direction.
If L' and B' are detected at the same time, it indicates the user intents to move in absolute backward B direction.
If B' and R' are detected at the same time, it indicates the user intents to move in the absolute rightward R direction.
If F' and L' are detected at the same time, it indicates the user intents to move in the absolute leftward L direction.

If $60°<\alpha<90°$:
If F' is detected, it indicates the user intents to move in the absolute leftward L direction.
If B' is detected, it indicates the user intents to move in the absolute rightwards R direction.
If R' is detected, it indicates the user intents to move in the absolute forward F direction.
If L' is detected, it indicates the user intents to move in absolute backward B direction.

It is thus possible to know the user's intention to move in the absolute directions F-B and L-R, which is important and practical in the rehabilitation purpose. Please note that the above algorithm is when the device of the invention is used in a right arm, as shown FIG. 3. In case the device is used in a right arm, the sign of the a angle would be the opposite.

As briefly outlined before, the portable device 100 of the present invention is advantageously used in a rehabilitation system, which is essentially composed of three principal elements: the portable device 100 used to support an upper limb of a user against gravity while allowing active or passive planar motion, a processing unit (which can be part of the portable device 100 or which can be implemented as a separate element), and a remote control and visualization unit (including the screen in front of the user). Moreover, a pad (with a textured polymer surface or polyester surface or similar) can be used to offer a suitable surface for the motion of the portable device 100. The pad can include some specifically designed obstacles or paths or three dimensional structures where the mobile device can be driven.

The portable device 100 of the invention, which comprises this means for detecting the user's intention to move and is applicable and particularly advantageous in games for rehabilitation.

These rehabilitation games usually have the necessary information to determine the next position of the portable device or the trajectory to be followed by the portable device. But in some cases the next position or the trajectory is not known (i.e. non-deterministic) because the patient can choose among different options. In these cases, detecting the user's intention to move is needed to determine the following target position.

Figure 14:
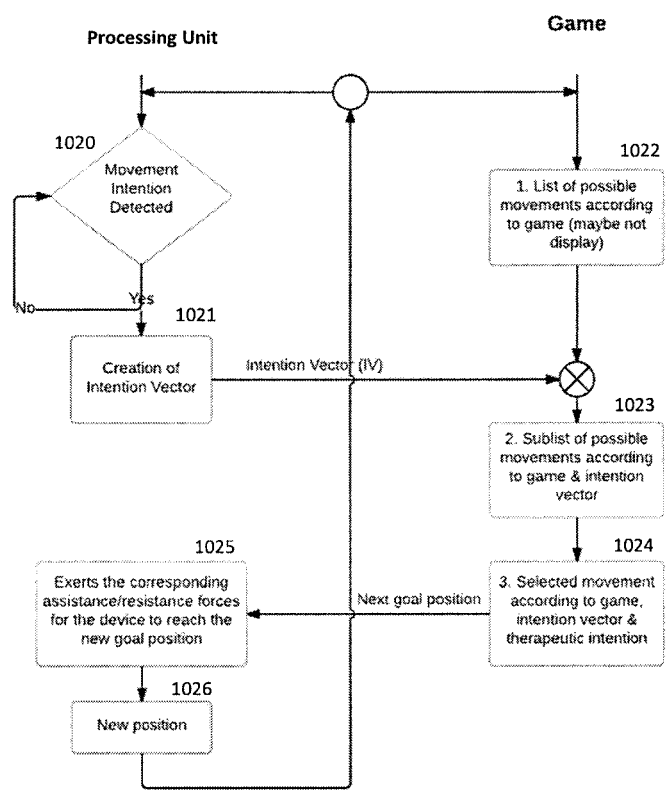
FIG. 14 is a flowchart showing how the present invention operates, and the interaction with a rehabilitation game.

In this case, FIG. 14 shows how the present invention operates, and how the processing unit interacts with the game.

It is first checked whether the processing unit has detected an intention to move by the user (1020), in which case the processing unit computes an intention vector (1021) which defines a direction of the user's movement intention. This vector is computed with the already computed intention of the user to move forward or backward and to move leftward or rightward either absolute or relative depending on purpose of the training game together with the position and orientation of the portable device 100 on the surface provided by the optical tracking device.

Usually the game has previously been configured to have different control points (corresponding to specific timings) where the user movement intention may be needed. Whenever one of those control points is reached a list of the most probable following target positions is computed (1022) according to the current state of the game and the current position and orientation of the portable device 100 (i.e. all the possible jigsaw puzzle pieces that can be selected from that position).

From that list of most probable target positions, a further selection is made (1023) with the positions whose linear trajectories from the current position present the biggest projections over the intention vector received from the processing unit.

From the selection made in the previous step (1023), if there are still several options, the one that provokes the best movement according to the therapeutic purposes is chosen. For example, in a specific user it is important to promote reaching movements (against flexor synergy), so if there is a doubt between two positions, the trajectory with the biggest projection over an optimal diagonal vector is selected (1024). The optimal diagonal vector is defined by the centre of the workspace (which is the rest position of the arm), and a point being at the maximum range of motion in a direction at 45° for a right arm, or at −45° for a left arm.

With the selected trajectory, assistive or resistive forces are applied to the portable device 100 by actuators inside so that the user reaches the target position (1025). The processing unit then computes (1026) the new position and the whole process is repeated.

Other possible therapeutic objectives in the rehabilitation exercises are:

Training for unilateral neglect rehabilitation: taking the furthest object in the affected side (calculating distance).

Training for the integration of both sides of the body: promoting crossing the medial line in each movement; that is, taking the furthest object in the opposite side of the midline.

The present invention provides means for actively involving the patient in the rehabilitation training, which is a very important factor in order to maximize training efficacy.

The portable device can include further load cells, so as to more finely detect the user's intention to move. Or it may further include other type of sensors, such as additional load cells, additional joint angles and/or more complex force sensors. It is also possible to improve detectability as well as to move in further directions besides the absolute and relative directions with additional sensors and artificial intelligent (AI) algorithms such as neural networks or genetic algorithms. For instance, in addition to signals from the load cells and the potentiometer, the measurement of EMG signals on the arm and precise cancellation of the noise due to tremor based on a learning scheme for each patient can enhance the quality of the detection while estimating more intended directions (such as forward-rightward, etc.) in both relative and absolute directions.

In this text, the term "comprises" and its derivations (such as "comprising", etc.) should not be understood in an excluding sense, that is, these terms should not be interpreted as excluding the possibility that what is described and defined may include further elements, steps, etc.

The invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention claimed is:

1. A portable device for rehabilitating an upper limb of a user, the portable device comprising:
   a support movable over a surface
   means for moving the support over the surface;
   a first support structure for supporting a forearm of the user;
   monitoring means for monitoring the movement of the support;
   a second support structure wherein the first support structure is coupled to the second support structure by means of a first joint having one rotational degree of freedom, the second support structure being coupled to the support by means of a second joint having three rotational degrees of freedom;
   a force sensing means for sensing a force exercised by an arm of the user on the support;
   angle sensor means for measuring an angle of inclination of the first support structure with respect to the second support structure; and
   processing means for detecting movement intention of the user based on the force measured by the force sensing means and on the angle of the first support structure.

2. The portable device of claim 1 wherein the one rotational degree of freedom of the first joint is pitch.

3. The portable device of claim 1 wherein the first support structure comprises first fastening means for fastening at least the forearm of a user.

4. The portable device of claim 3 wherein the first support structure further comprises second fastening means for fastening a wrist or a hand of the user, the first and second fastening means being located at separate points on the first support structure which define a first direction.

5. The portable device of claim 4 wherein the force sensing means comprises at least two load cells, wherein the at least two load cells are placed on the second support structure parallel to the first direction.

6. The portable device of claim 4 wherein the force sensing means comprises at least two load cells, wherein the at least two load cells are placed on the support symmetrically from a plane parallel to the first direction and which contains the first and second fastening means.

7. The portable device of claim 1 wherein the force sensing means are located between the second support structure and the support.

8. The portable device of claim 1 wherein the force sensing means comprises at least two load cells.

9. The portable device of claim 1 wherein the angle sensor means comprise a potentiometer mounted on the first joint.

10. The portable device of claim 1 wherein the processing means for detecting a movement intention of the user are configured to determine an intention of the user to move in a first direction and in one sense or the opposite within that first direction based on a value of the angle of the first support structure and its sign, respectively, as provided by the angle sensor means.

11. The portable device of claim 10 wherein the processing means for detecting a movement intention of the user are configured to determine an intention of the user to move in a first direction based on the angle of the first support structure and on the force measured by the force sensing means when the angle of the first support structure is above a pre-established value.

12. The portable device of claim 10 wherein the processing means are configured to produce an intention vector which defines a direction of the user's movement intention based on the intention of the user to move in the first direction and on the intention of the user to move in a second direction and on the position and orientation of the portable device on the surface provided by the monitoring means.

13. The portable device of claim 1 wherein the processing means for detecting a movement intention of the user are configured to determine an intention of the user to move in a second direction based on the force measured by the force sensing means.

14. A method for rehabilitating an upper limb of a user, the method comprising:
   attaching at least a portion the upper limb of the user to the portable device defined in claim 1;
   monitoring the movement of the support;
   measuring a force exercised by the upper limb of the user on the support;
   measuring an angle of inclination of the first support structure with respect to the second support structure; and
   detecting a movement intention of the user based on the force measured by the force sensing means and on the angle of the first support structure.

15. A rehabilitation system for an upper limb of a user, comprising:
   the portable device of claim 1;
   a remote control and visualization unit; and
   a training and assessment unit, which is configured to provide a training session; wherein the training and assessment unit is configured to determine a target position and orientation of the upper limb of the user based on an intention vector provided by the processing means and a set of possible target positions of the training session.

* * * * *